United States Patent
Rajagopalan et al.

(12)

(10) Patent No.: US 6,277,841 B1
(45) Date of Patent: Aug. 21, 2001

(54) QUINOLINE LIGANDS AND METAL COMPLEXES FOR DIAGNOSIS AND THERAPY

(75) Inventors: Raghavan Rajagopalan, Maryland Heights; Samuel I. Achilefu, St. Louis; Joseph E. Bugaj, St. Charles; Richard B. Dorshow, St. Louis, all of MO (US)

(73) Assignee: Mallinckrodt Inc., St. Louis, MO (US)

( * ) Notice: Subject to any disclaimer, the term of this patent is extended or adjusted under 35 U.S.C. 154(b) by 0 days.

(21) Appl. No.: 09/517,252

(22) Filed: Mar. 2, 2000

(51) Int. Cl.[7] .................. C07F 7/00; C07F 9/00
(52) U.S. Cl. ................. 514/185; 534/16; 546/7; 546/9; 546/10
(58) Field of Search ............ 546/7, 9, 10; 534/16; 514/185

(56) References Cited

FOREIGN PATENT DOCUMENTS

11288784 * 10/1999 (JP).

* cited by examiner

*Primary Examiner*—Richard L. Raymond
*Assistant Examiner*—Hong Liu
(74) *Attorney, Agent, or Firm*—Lawrence L. Limpus

(57) ABSTRACT

The present invention relates to novel ligands for forming metal complexes that absorb or fluoresce in the visible or near-infrared (NIR) region of the electromagnetic spectrum, new complexes incorporating such ligands, process for preparing such complexes, and methods of imaging or therapy using such agents. More particularly, the present invention specifically pertains to novel metal complexes derived from quinoline based heterocyclic $N_2O_3$, $N_3O_3$, $N_3O_4$, $N_3O_5$ and $N_2OS$ ligands, and are useful as general imaging, diagnostic, or therapeutic agents employing optical, nuclear medicine, or magnetic resonance procedures.

8 Claims, No Drawings

QUINOLINE LIGANDS AND METAL COMPLEXES FOR DIAGNOSIS AND THERAPY

FIELD OF THE INVENTION

The present invention relates to diagnosis and therapy within the field of biomedical optics. More particularly, the invention relates to novel ligands for forming metal complexes that absorb or fluoresce in the visible or near-infrared (NIR) region of the electromagnetic spectrum, new complexes incorporating such ligands, process for preparing such complexes, and methods of imaging or therapy using such agents.

BACKGROUND OF THE INVENTION

The field of biomedical optics is growing rapidly due to distinct advantages over other imaging modalities such as X-ray CT, MRI, nuclear medicine, or ultrasound (J. C. Hebden and D. T. Delpy. Diagnostic Imaging with Light, *The British Journal of Radiology*, 1997, 70, S206–S214; G. Freiherr. The Light Stuff: Optical Imaging in Medical Diagnostics, *Medical Devices & Diagnostic Industry*, 1998, 40–46). Compounds absorbing or emitting in the visible or NIR region of electromagnetic spectrum are potentially useful for tomographic imaging, endoscopic examination, photodynamic therapy, optoacoustic imaging, and sonoflourescene techniques. Furthermore, compounds absorbing or emitting in the appropriate visible region can be used to generate singlet oxygen and have been shown to be effective for photodynamic therapy of certain types of tumors.

Metal ions continue to play a major role in diagnostic and therapeutic medicine. For example, radionuclide metal complexes derived from both transition and lanthanide elements are being used extensively in diagnostic and therapeutic nuclear medicine procedures, paramagnetic complexes are being used extensively in magnetic resonance imaging procedures, and platinum complexes have long been used as cancer chemotherapeutic agents. Recently, metal complexes that absorb or emit in the visible or near-infrared (NIR) region have made a significant impact in the field of biomedical optics and have a great potential for photodiagnostic and phototherapeutic applications (J. N. Demas and B. A. DeGraff. Design and Applications of Highly Luminescent Transition Metal Complexes, *Analytical Chemistry*, 1991, 63, 829–837; M. P. Houline et al. Spectroscopic Characterization and Tissue Imaging Using Site-Selective Polyazacyclic Terbium (III) Chelates, *Applied Spectroscopy*, 1996, 50(10), 1221–1228; J. R. Lakowicz et al. Development of Long-Lifetime Metal-Ligand Probes for Biophysics and Cellular Imaging, *Journal of Fluorescence*, 1997, 7, 17–25; F. J. Steemers et al. Near-Infrared Luminescence of $Yb^{3+}$, $Nd^{3+}$, and $Er^{3+}$ Azatriphenylene Complexes, *Tetrahedron Letters*, 1998, 39, 7583–7586; G. E. Keifer and D. J. Bornhop. Fluorescent Chelates as Visual Tissue Specific Imaging Agents, U.S. Pat. No. 5,922,867, 1999). Examples of suitable metal ions for optical applications include Cr(III), Os(II), Ru(II), Ni(II), Eu(III), Tb(III), Lu(III), Yb(III), Er(III), and Nd(III). Eu(III), and Tb(III) are particularly preferred because of favorable absorption and emission properties in visible and NIR regions.

The key requirements for design of novel metal complexes for optical diagnostic and therapeutic application are: (a) strong absorption and emission in the visible or NIR region; (b) high thermodynamic, kinetic, and photo stability; (c) low toxicity; (d) water solubility; and (e) conjugation capability for targeted delivery to particular tissues or organs. Free metal ions are generally quite toxic; they need to be administered in the form of complexes with complexing agents (ligands) in order to deliver them to specific organs and to alleviate toxicity. Electronic property, toxicity, stability, and tissue specificity are greatly affected by the nature of the complexing agents (ligands). Various physicochemical and pharmacokinetic factors have to be considered in order to render the metal complex safe and effective. Electronic requirements for enabling the metal ion (transition and lanthanide) to absorb or emit in the visible or NIR region are well established and essentially involve incorporation of metal into highly polarizable π-electron rich, multidentate ligand systems. Energy transfer from aromatic donors (referred to as "antennae") to the lanthanide metal ion directly bounded to the donor group results in large increase in lanthanide fluorescence (S. I. Weissman, *Journal of Chemical Physics*, 1942, 10, 214; B. Alpha et al. Energy Transfer Luminescence of Europium (III) and Terbium (III) Cryptates of Macrobicyclic Polypyridine Ligands, *Angewandte Chemie International Edition in English*, 1987, 26(3), 266–267; J. B. Lamture et al. Luminescence Properties of Terbium (III) Complexes with 4-Substituted Dipiclolinic Acid Analogues, *Inorganic Chemistry*, 1995, 34, 864–869). In contrast, simple lanthanide metal salts or lanthanide ions coordinated to polyaminocarboxylate ligands wherein the aromatic donors are not directly attached exhibit very weak fluorescence in aqueous media (A. Abusaleh and C. F. Meares. *Photochemistry and Photobiology*, 1984, 39, 763–769). Long-wavelength fluorescence of transition metal complexes generally occurs via metal-to-ligand charge transfer (MCLT) interactions (Z. Murtaza and J. R. Lakowicz. Long-lifetime and Long-wavelength Osmium (II) Metal Complexes Containing Polypyridine Ligands. Excellent Red Fluorescent Dyes for Biophysics and for Sensors, *SPIE*, 1999, 3602, 309–315).

Toxicity of metal complexes is greatly affected by the nature of the ligands. Since in vivo release of free metal ions from the complex is a major cause of toxicity, thermodynamic and kinetic stability are critical requirements for the design of novel ligands. The thermodynamic stability constant indicates the affinity of totally unprotonated ligand for a metal ion. The conditional stability constant indicates the stability of the complex under physiological pH. Ion selectivity of the ligand toward the desired metal ion over other endogenous metal ions such as zinc, iron, magnesium, and calcium, determines the rate of release of the metal ion into the vascular or extracellular space. The released metal ion is capable of crossing the blood-brain barrier and thereby perturbing the neurophysiology. Therefore, in vivo reaction kinetics are also a major factor in the design of stable complexes and complexes with structural features that make in vivo transmettlation reactions proceed much slower than the biological clearance of the intact metal complexes would be predicted to have low toxicities (W. Cacheris et al., *Magnetic Resonance Imaging*, 1990, 8, 467; Oksendal et al., *Journal of Magnetic Resonance Imaging*, 1993, 3, 157). Thus, a need continues to exist for new and structurally diverse metal complexes for use as imaging, diagnostic, or therapeutic agents employing optical procedures.

SUMMARY OF THE INVENTION

Thermodynamically and kinetically stable metal complexes can be achieved with a proper choice of ligands systems. Transition metal ions generally require soft donors such as thiols and phosphines, whereas lanthanide ions require hard donors such as carboxylates or amines. However, unsaturated heterocyclic bases such as pyridines, imidazoles, and the like are excellent coordinators to both types of metal ions. Numerous pyridine, quinoline, and imidazole based metal complexes have been prepared and many of them have been conjugated to bioactive carriers such as immunoglobulins (R. Rajagopalan et al. Preparation, Characterization, and Biological Evaluation of Technetium (V) and Rhenium (V) Complexes of Novel Heterocyclic Tetradentate $N_3S$ Ligands, *Bioconjugate Chemistry*, 1997, 8, 407–415; J. B. Lamture and T. G. Wensel. A Novel Reagent for Labeling Macromolecules with Intensely Luminescent Lanthanide Complexes, *Tetrahedron Letters*, 1993, 34(26), 4141–4144). The present invention specifically pertains to novel quinoline based heterocyclic $N_2O_3$, $N_3O_3$, $N_3O_4$, and $N_2OS$ ligands that are suitable for complexing metal ions, and are useful as general imaging, diagnostic, or therapeutic agents employing optical, nuclear medicine, or magnetic resonance procedures. The principal advantages of this invention are: (a) the metal ion is directly bounded to the "antenna" portion of the molecule, and (b) the entire complex is rigid. Both of these factors are expected to contribute to significant enhancement of absorption and luminescence properties compared to those metal complexes where the antenna is either located remote from the metal ion or has considerable degrees of freedom.

DETAILED DESCRIPTION OF THE INVENTION

The present invention provides new and structurally diverse compositions comprising complexing agents (ligands) of the general Formula 1,

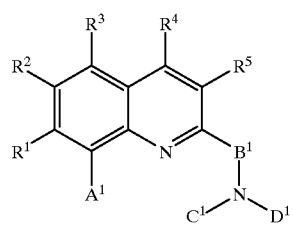

Formula 1 wherein $R^1$ to $R^5$ may the same or different and are selected from the group consisting of hydrogen, C1–C10 alkyl, —OH, C1–C10 polyhydroxyalkyl, C1–C10 alkoxyl, C1–C10 alkoxyalkyl, —$SO_3H$, —$(CH_2)_m$—$CO_2H$ and —$NR^6R^7$; $R^6$ and $R^7$ may the same or different and are selected from the group consisting of hydrogen, C1–C10 alkyl, C1–C10 aryl, and C1–C10 polyhydroxyalkyl; m ranges from 0 to 10; $A^1$ is selected from the group consisting of —OH, —$CO_2H$, —$N(R^8)(R^9)$, —SPg —$CONHR^{10}$ and —$HNCOR^{11}$; $R^8$ and $R^9$ may the same or different and are selected from the group consisting of hydrogen, C1–C10 alkyl, C1–C10 aryl, C1–C10 polyhydroxyalkyl, —$(CH_2)_mCO_2H$ and —$(CH_2)_2$—$N(CH_2CO_2H)_2$; $R^{10}$ is selected from the group consisting of hydrogen, C1–C10 alkyl, C1–C10 aryl, C1–C10 polyhydroxyalkyl and —$(CH_2)_2$—SPg; $R^{11}$ is selected from the group consisting of hydrogen, C1–C10 alkyl, C1–C10 aryl, C1–C10 polyhydroxyalkyl and —CH($R^{12}$)—SPg; $R^{12}$ is selected from the group consisting of hydrogen, C1–C10 alkyl, C1–C10 aryl, C1–C10 polyhydroxyalkyl, —$(CH_2)_mCO_2H$ and —$(CH_2)_nNH_2$; n varies from 1 to 10; $B^1$ is selected from the group consisting of —$CHR^{13}$ and —CH($R^{14}$)CH($R^{15}$); $R^{13}$ to $R^{15}$ may be the same or different and are defined in the same manner as $R^{12}$; $C^1$ is selected from the group consisting of hydrogen, C1–C10 alkyl, C1–C10 aryl, C1–C10 polyhydroxyalkyl, C1–C10 alkoxyl, C1–C10 alkoxyalkyl, —$(CH_2)_mCO_2H$, —$CH_2CH_2$—$N(CH_2CO_2H)_2$, —$(CH_2)_2$—SPg and —COCH($R^{16}$)—SPg; $R^{16}$ is defined in the same manner as $R^{12}$; $D^1$ is selected from the group consisting of hydrogen, C1–C10 alkyl, C1–C10 aryl, hydroxyl, C1–C10 polyhydroxyalkyl, C1–C10 alkoxyl, C1–C10 alkoxyalkyl, —$(CH_2)_mCO_2H$, and —$CH_2CH_2$—$N(CH_2CO_2H)_2$; and Pg may be hydrogen or a protecting group selected from the group consisting of t-butyl, benzyl, benzoyl, 2,4-dimethoxybenzyl, trityl, tetrahydropyranyl, C1–C10 acyl, C1–C10 alkoxyalkyl, and C1–C10 alkoxycarbonyl.

In a preferred embodiment, ligands according to the present invention have the general formula of Formula 1 above wherein $R^1$ to $R^5$ are selected from the group consisting of hydrogen, —OH, C1–C10 alkoxyl, —$(CH_2)_m$—$CO_2H$, and —$N(R^6)(R^7)$; $A^1$ is selected from the group consisting of —OH, —$N(R^8)(R^9)$, and —$HNCOR^{11}$; $B^1$ is —$CHR^{13}$; $C^1$ is selected from the group consisting of hydrogen, C1–C10 alkyl, —$(CH_2)_mCO_2H$, —$CH_2CH_2$—$N(CH_2CO_2H)_2$, and —COCH($R^{16}$)—SPg; $D^1$ is selected from the group consisting of hydrogen, C1–C10 alkyl, C1–C10 polyhydroxyalkyl, —$(CH_2)_m$—$CO_2H$, and —$CH_2CH_2$—$N(CH_2CO_2H)_2$; and Pg is selected from the group consisting of C1–C10 acyl, tetrahydropyranyl, C1–C10 alkoxyalkyl, and C1–C10 alkoxycarbonyl.

In a further preferred embodiment, ligands according to the present invention have the general formula of Formula 1 above wherein $R^1$ to $R^5$ are hydrogens; $A^1$ is —OH or —$N(CH_2CO_2H)_2$; $B^1$ is —$CH_2$—; $C^1$ is selected from the group consisting of —$CH_2$—$CO_2H$, —$CH_2CH_2$—$N(CH_2CO_2H)_2$, and —$COCH_2$—SPg; $D^1$ is selected from the group consisting of hydrogen, C1–C10 alkyl, and —$CH_2$—$CO_2H$; and Pg is selected from the group consisting of benzoyl, tetrahydropyranyl, and methoxycarbonyl.

The present invention also provides structurally diverse compositions comprising metal complexes of the general formula of Formula 2 formed by coordination of an appropriate metal ion to the ligands derived from Formula 1 shown above,

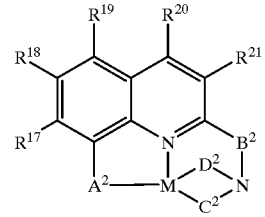

Formula 2 wherein $R^{17}$ to $R^{21}$ may the same or different and are defined in the same manner as $R^1$; $A^2$ is selected from the group consisting of —$O^-$, —$CO_2^-$, —$N(R^8)(R^9)$, —SPg —CON($R^{10}$), and —$NCOR^{11}$; $R^8$ and $R^9$ may the same or different and are selected from the group consisting of hydrogen, C1–C10 alkyl, C1–C10 aryl, C1–C10 polyhydroxyalkyl, —$(CH_2)_mCO_2^-$, and —$(CH)_2$—$N(CH_2CO_2^-)_2$; $R^{10}$ is selected from the group consisting of hydrogen, C1–C10, alkyl, C1–C10 aryl, C1–C10 polyhydroxyalkyl, and —$(CH_2)_2$—S; $R^{11}$ is selected from the group consisting of hydrogen, C1–C10 alkyl, C1–C10 aryl, C1–C10 polyhydroxyalkyl, and —CH($R^{12}$)—$S^{31}$ ; $R^{12}$ is selected from the group consisting of hydrogen, C1–C10 alkyl, C1–C10 aryl, C1–C10 polyhydroxyalkyl, —$(CH_2)_mCO_2^-$ and —$(CH_2)_nNH_2^-$; m ranges from 0 to 10 n varies from 1 to 10; $B^2$ is selected from the group consisting of —$CHR^{13}$ and —CH($R^{14}$)CH($R^{15}$); $R^{13}$ to $R^{15}$ may be the same or different and are defined in the same manner as $R^{12}$; $C^2$ is selected from the group consisting of hydrogen, C1–C10 alkyl, C1–C10 aryl, C1–C10 polyhydroxyalkyl, C1–C10 alkoxyl, C1–C10 alkoxylalkyl, —$(CH_2)mCO_2^-$, —$CH_2CH_2$—$N(CH_2CO_2^-)_2$, —$(CH_2)_2$—$S^-$, and —COCH$(R^{16})$—$S^-$; $R^{16}$ is defined in the same manner as $R^{12}$, $D^2$ is selected from the group consisting of hydrogen, C1–C10 alkyl, C1–C10 aryl, hydroxyl, C1–C10 polyhydroxyalkyl, C1–C10 alkoxyl, C1–C10 alkoxylalkyl, —$(CH_2)_mCO_2^-$, and —$CH_2CH_2$—$N(CH_2CO_2^-)_2$ and M is a metal ion having an atomic number of $_{24}$ to 31, 42 to 49, 58–71, or 74–83.

In a preferred embodiment, the complexes according to the present invention have the general formula of Formula 2 above wherein $R^{17}$ to $R^{21}$ are selected from the group consisting of hydrogen, —$O^-$, C1–C10 alkoxyl, —$(CH2)_m$—$CO_2^-$; and —$N(R^6)(R^7)$; $A^2$ is selected from the group consisting of —$O^-$; —$N(R^8)(R^9)$, and —$HNCOR^{11}$; $B^2$ is —$CHR^{13}$; $C^2$ is selected from the group consisting of hydrogen, C1–C10 alkyl, —$(CH_2)mCO_2^-$, —$CH_2CH_2$—$N(CH_2CO_2^-)_2$, and —$COCH(R^{16})$—$S^-$; $D^2$ is selected from the group consisting of hydrogen, C1–C10 alkyl, C1–C10 polyhydroxyalkyl, —$(CH_2)mCO_2^-$, and —$CH_2CH_2$—$N(CH_2CO_2^-)_2$ and M is a metal ion having an atomic number of 24 to 28, 31, 42 to 45, 49, 62–65, 71, 75, 76, or 83.

In a further preferred embodiment, the complexes according to the present invention have the general formula of Formula 2 above wherein $R^{17}$to $R^{21}$ are hydrogens; $A^2$ is —$O^-$ or —$N(CH_2CO_2^-)_2$; $B^2$ is —$CH_2$—; $C^2$ is selected from the group consisting of —$CH_2$—$CO_2^-$, —$CH_2CH_2$—$N(CH_2CO_2^-)_2$, and —$COCH_2$—$S^-$; $D^2$ is selected from the group consisting of hydrogen, C1–C10 alkyl, and —$CH_2$—$CO_2^-$; and M is a metal ion having an atomic number of 24–26, 28, 31, 43, 44, 49, 62–65, 71, 75, or 76.

The compositions of the invention are suitable for use with a variety of other modalities including X-rays, magnetic resonance, and radiographic imaging. Electron donating and electron releasing groups at various positions in the ligands of Formula 1 and the metal complexes Formula 2 provide an opportunity to alter the absorption and emission properties of the molecule thereby enhancing the optical utility of these molecules. Also, these additional functionalities afford the capability of conjugation to biomolecules and synthetic polymers for selective delivery to various organs or tissues of interest. The term biomolecule refers to all natural and synthetic molecules that play a role in biological systems. Biomolecules include hormones, amino acids, peptides, peptidomimetics, proteins, nucleosides, nucleotides, nucleic acids, carbohydrates, lipids, albumins, mono- and polyclonal antibodies, receptor molecules, receptor binding molecules, synthetic polymers, and aptamers. Specific examples of biomolecules include inulins, prostaglandins, growth factors, growth factor inhibitors like somatostatin, liposomes, and nucleic acid probes. Example of synthetic polymers include polylysine, polyaspartic acid, polyarginine, aborols, dendrimers, and cyclodextrins. The advantages of biomolecules include enhance tissue targeting through specificity and delivery. The specific targeting of effector molecules to a particular tissue, such as tumor, using antibodies is well known in the art (see Halpern et al., *Diagnostic Imaging*, 1983, 40). Coupling of bifunctional ligands and complexes to biomolecules can be accomplished by several known methods (see Hnatowich et al., *Science*, 1983, 220, 613).

The complexes of the present invention may vary widely depending on the contemplated application. For diagnostic imaging of areas of lesion, fluorescent compounds absorbing and emitting in the near infrared (NIR) region, i.e. 650–900 nm, are desirable. For monitoring blood clearance or for endoscopic examination of lesions, dyes absorbing and emitting in the region of 350–950 nm, preferably 600–900 nm, are desirable. Similarly, the carrier molecules may also vary widely. For blood persistent agents, albumin or methylated serum albumin is preferable. For renal function measurements, polysaccharides or anionic polypeptides are desirable. For endoscopic examination of lesions, antibodies, peptides, or carbohydrates directed against specific cell surface markers are preferred.

Diagnostic compositions comprising the compounds of the invention are also provided. Methods of performing diagnostic procedures with compositions of the invention are also disclosed. The method comprises administering an effective amount of a composition of the invention contained in a pharmaceutically acceptable formulation to a patient either systemically or locally to the organ or tissue to be studied. It is believed that the novel compositions of the present invention have broad clinical utility, which includes, but is not limited to, diagnostic imaging of tumors, of inflammation (both sterile and bacterial), and of impaired vasculature; laser guided endoscopic examination of sites of lesion; and photodynamic and chemotherapy of tumors or infection.

The novel compositions of this invention can be formulated into diagnostic or therapeutic compositions for enteral, parenteral, or oral administration. These compositions contain an effective amount of the metal complexes along with conventional pharmaceutical carriers and excipients appropriate for the type of administration contemplated. These compositions may also include stabilizing agents selected from the class consisting of mono- or polycarboxylic acids, mono- or polyamines, mono- or polynucleotides, mono or polysaccharides, amino acids, and peptides. For example, parenteral administration advantageously contains a sterile aqueous solution or suspension of the complexes whose concentration ranges from about 1 nM to about 0.5 M. Preferred parenteral formulations have a concentration of 1 $\mu$M to 10 mM. Such solutions also may contain pharmaceutically acceptable buffers, emulsifiers, surfactants, and, optionally, electrolytes such as sodium chloride. Concentrations of the metal complexes of this invention in formulations for enteral administration may vary widely as is well-known in the art. In general, such formulations are liquids which include an effective amount of the complexes in aqueous solution or suspension. Such enteral composition may optionally include buffers, surfactants, emulsifiers, thixotropic agents, and the like. Compositions for oral administration may also contain flavoring agents and other ingredients for enhancing their organoleptic qualities. The diagnostic compositions are administered in doses effective to achieve the desired diagnostic or therapeutic objective. Such doses may vary widely depending upon the particular complex employed, the organs or tissues to be examined, the equipment employed in the clinical procedure, and the like.

The following examples illustrate specific embodiments of this invention. As would be apparent to skilled artisans, various changes and modifications are possible and are contemplated within the scope of the invention described.

EXAMPLE 1

Preparation of the Quinoline Ligand (Formula 3)

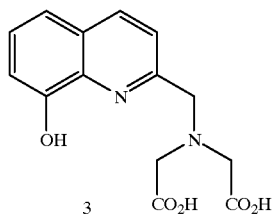

Formula 3

A mixture of 2-aminomethyl-8-hydroxyquinoline hydrochloride (Chem-Master International) (2.1 g, 10 mmol), t-butyl bromoacetate (3.9 g, 20 mmol), diisopropylethylamine (3.9 g, 30 mmol), and sodium iodide (0.15 g, 1 mmol) in dimethoxyethane (20 mL) was heated under reflux for 2 hours. The reaction mixture was poured onto water and extracted with ethyl acetate (3×30 mL). The combined organic layers were washed with water (3×50 mL), dried ($Na_2SO_4$), filtered, and the filtrate evaporated in vacuo to furnish 2.2 g of the diester as a red gum. $^1$H-NMR ($CDCl_3$) δ8.17 (s, 1H), 7.60 (d, 1H), 7.40 (d, 1H), 7.35 (m, 2H), 7.15 (d, 1H), 4.18 (s, 2H), 3.50 (s, 4H); $^{13}$C-NMR ($CDCl_3$) δ165.7, 152.7, 147.2, 137.8, 122.4, 117.4, 112.8, 105.0, 76.4, 55.0, 50.9, 23.3.

The diester obtained above was treated with 96% formic acid (20 mL) and kept at ambient temperature for 24 hours. Excess formic acid was removed by evaporation in vacuo and the brown residue was treated with water (25 mL), and filtered hot (gravity filtration). Upon cooling, the product crystallized as a red solid which was filtered and dried to furnish 1.1 g of the ligand of Formula 3. $^1$H-NMR (DMSO-$d_6$) δ9.45 (broad, 2H), 8.15 (d, 1H), 7.77 (d, 1H), 7.28 (m, 2H), 7.10 (d, 1H), 4.15 (s, 2H), 3.50 (s, 4H); $^{13}$C-NMR (DMSO-$d_6$) δ172.5, 158.1, 152.8, 137.4, 136.4, 127.9, 127.0, 121.5, 117.6, 111.3, 59.7, 54.5; electrospray mass spectrum, m/Z=291 (M+H).

EXAMPLE 2

Preparation of the Chromium Complex (Formula 4)

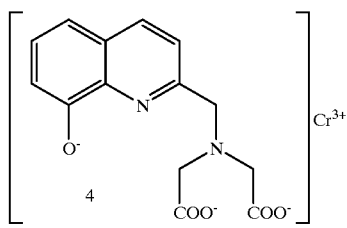

Formula 4

A solution of the ligand of Formula 3 (145 mg, 0.5 mmol) and chromium acetylacetonate (175 mg, 0.5 mmol) in dimethylformamide (2 mL) was treated with two drops of water and two drops of 96% formic acid and the entire mixture was heated at 100–120° C. for 24 hours. After cooling the reaction mixture to ambient temperature, the solution was poured onto ethyl ether. The brown precipitate was collected by filtration, washed with ether, dried, and recrystallized from propanol to give the chromium complex of Formula 4 as a brown solid.

EXAMPLE 3

Hypothetical Preparation of the Iron Complex (Formula 5)

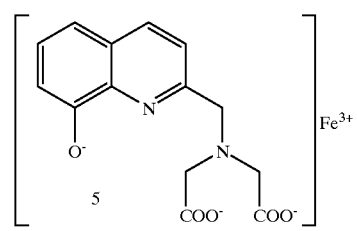

Formula 5

A solution of the ligand of Formula 3 (145 mg, 0.5 mmol) and iron acetylacetonate (177 mg, 0.5 mmol) in dimethylformamide (2 mL) is treated with two drops of water and the entire mixture is heated at 100–120° C. for 16 hours. After cooling the reaction mixture to ambient temperature, the solution is poured onto ethyl ether. The precipitate is collected by filtration and is purified by either recrystallization or C-18 reverse phase chromatography to give the iron complex of Formula 5.

EXAMPLE 4

Preparation of Ruthenium Complex (Formula 6)

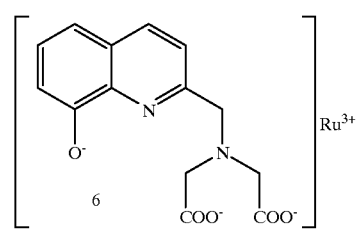

Formula 6

A solution of the ligand of Formula 3 (145 mg, 0.5 mmol) and ruthenium acetylacetonate (199 mg, 0.5 mmol) in dimethylformamide (2 mL) was treated with two drops of water and the entire mixture was heated at 100–120° C. for 16 hours. After cooling the reaction mixture to ambient temperature, the solution was poured onto ethyl ether. The brown precipitate was collected by filtration, washed with ether, dried, and recrystallized from propanol to give the ruthenium complex of Formula 6 as a black solid.

EXAMPLE 5

Preparation of the Quinoline Ligand (Formula 7)

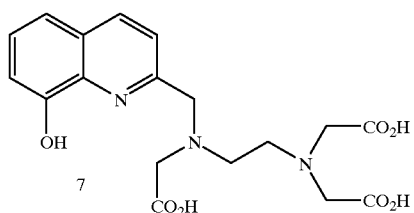

Formula 7

A mixture of 2-chloromethyl-8-hydroxyquinoline hydrochloride (Chem-Master International) (0.69 g, 3 mmol), ethylenediamine-N,N,N'-triacetic acid tri(t-butyl)ester (10.8 g, 3 mmol), diisopropylethylamine (0.78 g, 6 mmol), and sodium iodide (0.15 g, 1 mmol) in dimethoxyethane (10 mL) was heated under reflux for 4 hours. The reaction mixture was poured onto water and extracted with ether (3×30 mL). The combined organic layers were washed with water (3×50 mL), dried ($Na_2SO_4$), filtered, and the filtrate evaporated in vacuo to furnish the triester which was purified by silica gel chromatography using chloroform-methanol (9:1) as eluent. $^1$H-NMR ($CDCl_3$) δ8.10 (d, 1H), 7.61 (d, 1H), 7.32 (m, 2H), 7.08 (d, 1H), 4.08 (s, 2H), 3.42 (s, 4H), 3.38 (s, 4H), 2.83 (bs, 4H); $^{13}$C-NMR ($CDCl_3$) δ170.6, 158.0, 152.1, 137.4, 136.3, 127.5, 127.1, 122.1, 117.5, 112.8, 109.9, 80.9, 80.8, 60.4, 56.1, 55.8, 52.5, 51.8.

The triester obtained above (820 mg) was treated with 96% formic acid (10 mL) and heated at 80–90° C. for 15 minutes and thereafter kept at ambient temperature for 24 hours. Excess formic acid was removed by evaporation in vacuo and the residue was triturated with acetone (50 mL). The solid was collected by filtration and dried to give 520 mg of the ligand of Formula 7 as a pale pink solid. $^1$H-NMR (DMSO-$d_6$) δ8.15 (d, 1H), 7.60 (d, 1H), 7.32 (m, 2H), 7.05 (d, 1H), 4.25 (s, 2H), 3.42 (s, 4H), 3.38 (s, 4H), 2.80 (bs, 4H); $^{13}$C-NMR (DMSO-$d_6$) δ172.4, 171.3, 156.2, 152.8, 137.3, 136.6, 127.8, 127.2, 121.4, 117.6, 111.2, 59.3, 55.0, 54.8, 51.7, 50.9; electrospray mass spectrum, m/Z=392 (M+H).

EXAMPLE 6

Preparation of Europium Complex (Formula 8)

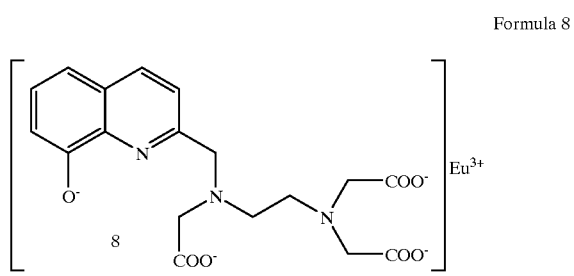

Formula 8

A mixture of the ligand of Formula 7 (780 mg, 2 mmol) and europium oxide (352 mg, 1 mmol) in deionized, distilled water (10 mL) was heated under reflux for 72 hours. The mixture remained heterogeneous throughout the heating period. The precipitate was filtered, washed with water and dried to give the europium complex of Formula 8 as an off-white solid.

EXAMPLE 7

Hypothetical Preparation of Lutetium Complex (Formula 9)

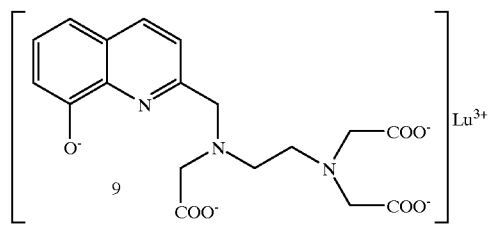

Formula 9

A mixture of the ligand of Formula 7 (798 mg, 2 mmol) and lutetium oxide (398 mg, 1 mmol) in deionized, distilled water (10 mL) is heated under reflux for 24 hours. The solution is filtered through fine porosity sintered glass funnel to remove undissolved impurities and the filtrate is poured onto acetone (200 mL). The precipitate is collected, washed with acetone, and dried. The crude lutetium complex of Formula 9 is purified by C-18 reverse phase chromatography.

EXAMPLE 8

Preparation of Iron Complex (Formula 10)

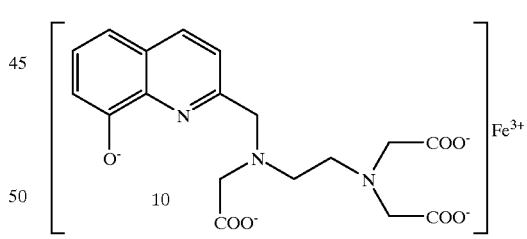

Formula 10

A solution of the ligand of Formula 7 (391 mg, 1 mmol) in 1N sodium hydroxide was treated with ferric chloride hexahydrate (269 mg, 1 mmol) and the entire mixture was stirred at ambient temperature for 16 hours. The dark reaction mixture was filtered and the filtrate washed with ice-cold water and dried. The U.V. spectrum showed intense bands at 455 nm and 596 nm. The mass spectrum showed the correct molecular ion for the iron complex of Formula 10, m/Z=445 (M+H).

EXAMPLE 9

Hypothetical Preparation of the Gadolinium Complex (Formula 11)

Formula 11

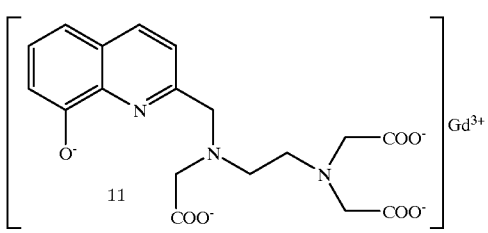

A mixture of the ligand of Formula 7 (780 mg, 2 mmol) and gadolinium oxide (362 mg, 1 mmol) in deionized, distilled water (10 mL) is heated under reflux for 24 hours. The solution is filtered through fine porosity sintered glass funnel to remove undissolved impurities and the filtrate is poured onto acetone (200 mL). The precipitate is collected, washed with acetone, and dried. The crude gadolinium complex of Formula 11 is purified by C-18 reverse phase chromatography.

EXAMPLE 10

Preparation of the Quinoline Ligand (Formula 12)

Formula 12

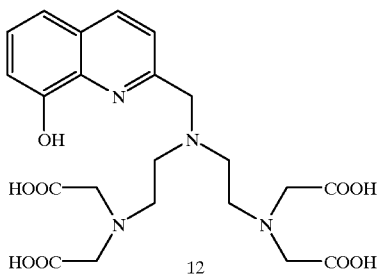

A mixture of 2-chloromethyl-8-hydroxyquinoline hydrochloride (1.05 g, 5 mmol), di-t-butyl 3,10-bis(t-butoxycarbonylmethy)-3,6,10-triazadodecanedioate (1.78 g, 1 mmol), diisopropylethylamine (3.87 g, 20 mmol), and sodium iodide (0.15 g, 1 mmol) in dimethoxyethane (10 mL) was heated under reflux for 4 hours. The reaction mixture was poured onto water and extracted with ethyl ether (3×20 mL). The combined organic layers were washed with water (3×20 mL), dried ($Na_2SO_4$), filtered, and the filtrate evaporated in vacuo to furnish the tetraester which was purified by silica gel chromatography using chloroform-methanol (9:1). The yield of the pale brown tetraester was 1.8 g. $^1$H-NMR ($CDCl_3$) δ8.02 (d, 1H), 7.61 (d, 1H), 7.38 (m, 2H), 7.25 (d, 1H), 7.15 (d, 1H), 3.95 (s, 2H), 3.42 (bs, 8H), 2.90 (m, 4H), 2.72 (bs, 4H), 1.21 (s, 48H); $^{13}$C-NMR ($CDCl_3$) δ170.6, 158.7, 152.1, 137.4, 136.2, 127.5, 127.0, 122.0, 117.5, 112.8, 109.9, 80.8, 60.8, 56.1, 53.0, 51.8, 28.1.

The tetraester obtained above was treated with 96% formic acid (10 mL) and kept at ambient temperature for 24 hours. The reaction mixture was poured onto acetone (200 mL) and solid was collected by filtration and dried to furnish the ligand of Formula 12 as an off-white solid. $^1$H-NMR (DMSO-$d_6$) δ8.32 (d, 1H), 7.58 (d, 1H), 7.38 (m, 2H), 7.05 (d, 1H), 4.58 (bs, 2H), 3.37 (bs, 8H), 3.12 (bs, 4H), 3.00 (bs, 4H); $^{13}$C-NMR (DMSO-$d_6$) δ173.0, 153.1, 152.4, 137.2, 136.6, 137.0, 127.8, 127.7, 121.3, 117.4, 111.5, 58.0, 55.6, 51.7, 49.7; elecctrospray mass spectrum, m/Z=493 (M+H).

EXAMPLE 11

Preparation of the Europium Complex (Formula 13)

Formula 13

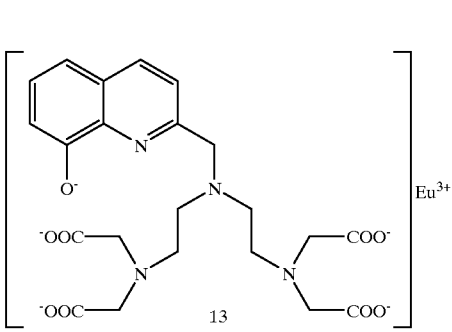

A mixture of the ligand of Formula 12 (984 mg, 2 mmol) and europium oxide (352 mg, 1 mmol) in deionized, distilled water (10 mL) was heated under reflux for 24 hours. The solution was filtered through a fine porosity sintered glass funnel to remove undissolved impurities and the filtrate was poured onto acetone (200 mL). The yellow-orange solid precipitate, a crude europium complex of Formula 13, was collected, washed with acetone, and dried.

EXAMPLE 12

Hypothetical Preparation of the Lutetium Complex (Formula 14)

Formula 14

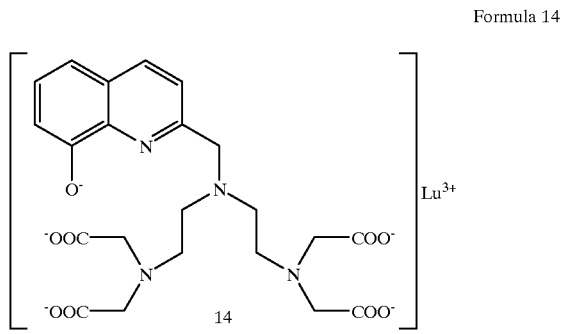

A mixture of the ligand of Formula 12 (984 mg, 2 mmol) and lutetium oxide (398 mg, 1 mmol) in deionized, distilled water (10 mL) is heated under reflux for 24 hours. The solution is filtered through fine porosity sintered glass funnel to remove undissolved impurities and the filtrate is poured onto acetone (200 mL). The precipitate is collected, washed with acetone, and dried. The crude lutetium complex of Formula 14 is purified by C-18 reverse phase chromatography.

EXAMPLE 13

Hypothetical Preparation of the Chromium Complex (Formula 15)

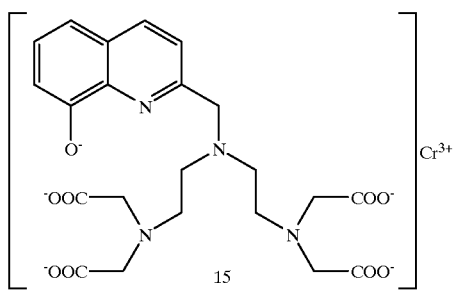

Formula 15

A mixture of the ligand of Formula 12 (390 mg, 1 mmol) and chromium acetylacetonate (350 mg, 1 mmol) in dimethylformamide (3 mL) is treated with two drops of water and the entire mixture was heated at 100–120° C. for 24 hours. After cooling the reaction mixture to ambient temperature, the solution is poured onto ethyl ether. The precipitate is collected by filtration, washed with ether, and dried. The crude chromium complex of Formula 15 is purified by crystallization or C-18 reverse phase chromatography.

EXAMPLE 14

Hypothetical Preparation of Gadolinium Complex (Formula 16)

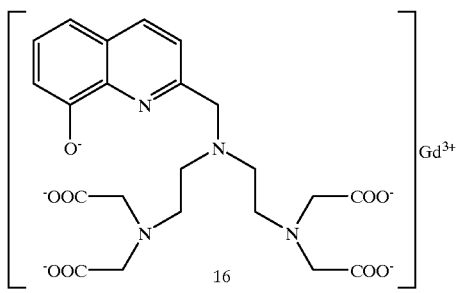

Formula 16

A mixture of the ligand of Formula 12 (780 mg, 2 mmol) and gadolinium oxide (362 mg, 1 mmol) in deionized, distilled water (10 mL) is heated under reflux for 24 hours. The solution is filtered through a fine porosity sintered glass funnel to remove undissolved impurities and the filtrate is poured onto acetone (200 mL). The precipitate is collected, washed with acetone, and dried. The crude gadolinium complex of Formula 16 is purified by C-18 reverse phase chromatography.

EXAMPLE 15

Preparation of the Quinoline Ligand (Formula 17)

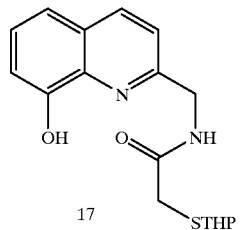

Formula 17

A mixture of 2-aminomethyl-8-hydroxyquinoline hydrochloride (1.05 g, 5 mmol) N-succinimidyl S-tetrahydropyranylmercaptoacetate (1.37 g, 5 mmol), and triethylamine (0.51 g, 5 mmol) in acetonitrile (15 mL) was heated under reflux for 2 hours. The reaction mixture was poured onto water and extracted with methylene chloride (3×20 mL). The combined organic layers were washed with water and dried ($MgSO_4$) to give the ligand of Formula 17 as an orange gum which was sufficiently pure for complexation purposes. $^1$H-NMR ($CDCl_3$) δ8.42 (broad, 1H), 8.20 (d, 1H), 7.41 (d, 1H), 7.35 (m, 2H), 7.18 (d, 1H), 4.95 (dd, 1H), 4.82(dd, 1H), 4.73 (dd, 1H), 4.00 (m, 1H), 3.78 (m, 1H), 3.57 (d, 1H), 3.35 (d, 1H), 2.10–1.55 (m, 6H); $^{13}$C-NMR ($CDCl_3$) δ169.6, 154.1, 152.1, 137.0, 136.9, 127.5, 127.4, 120.2, 117.8, 110.9, 83.7, 65.5, 44.7, 35.2, 30.8, 25.0, 21.6.

EXAMPLE 16

Preparation of Rhenium Complex (Formula 18)

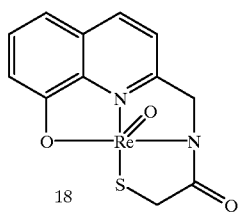

Formula 18

A mixture of the ligand of Formula 17 (332 mg, 1 mmol), triethylamine (2 drops), and oxodichlorobis(triphenyl) phosphinoethoxyrhenium (880 mg, 1 mmol) in ethanol (5 ml) was heated under reflux for 6 hours. The precipitate was collected by filtration and the crude rhenium complex of Formula 18 was purified by recrystallization.

While the invention has been disclosed by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

We claim:

1. A composition comprising a quinoline metal complex of Formula II:

Formula II

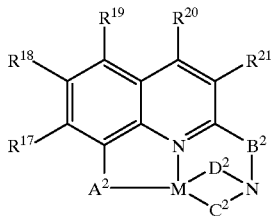

wherein $R^{17}$ to $R^{21}$ may be the same or different and are selected from the group consisting of hydrogen, C1–C10 alkyl, —OH, C1–C10 polyhydroxyalkyl, C1–C10 alkoxyl, C1–C10 alkoxyalkyl, —SO$_3$H, —(CH$_2$)m—CO$_2$H, and —NR$^6$R$^7$; A$^2$ is selected from the group consisting of —O—, —CO$_2^-$, —N(R$^8$)(R$^9$), —SPg —CON(R$^{10}$), and NCOR$^{11}$; R$^8$ and R$^9$ may be the same or different and are selected from the group consisting of hydrogen, C1–C10 alkyl, C1–C$^{10}$ aryl, C1–C$^{10}$ polyhydroxyalkyl, —(CH$_2$)$_m$CO$_2^-$, and —(CH$_2$)$_2$—N(CH$_2$CO$_2^-$)$_2$; R$^{10}$ is selected from the group consisting of hydrogen, C1–C10 alkyl, C1–C10 aryl, C1–C10 polyhydroxyalkyl, and —(CH$_2$)$_2$— S; R$^{11}$ is selected from the group consisting of hydrogen, C1–C$^{10}$ alkyl, C1–C$^{10}$ aryl, C1–C10 polyhydrcoxyalkyl, and —CH(R$^{12}$)—S$^-$; R$^{12}$ is selected from the group consisting of hydrogen, C1–C10 alkyl, C1–C10 alkyl, C1–C10 polyhydroxyalkyl, —(CH$_2$)mCO$_2$ and —(CH$_2$)nNH$_2$; m ranges from 0 to 10 and n varies from 1 to 10; B$^2$ is selected from the group consisting of —CHR$^{13}$ and —CH(R$^{14}$)CH(R$^{15}$), R$^{13}$ to R$^{15}$ may be the same or different and are selected from the group consisting of hydrogen, C1–C10 alkyl, C1–C10 aryl, C1–C10 polyhydroxyalkyl, —(CH$_2$)m—CO$_2$ and —(CH$_2$)$_n$NH; C$^2$ is selected from the group consisting of hydrogen, C1–C10 alkyl, C1–C10 aryl, C1–C10 polyhydroxyalkyl, C1–C10 alkoxyl, C1–C10 alkoxyalkyl, —(CH$_2$)$_m$, CO$_2$, —CH$_2$CH$_2$—N(CH$_2$)$_m$CO$_2^-$; —(CH$_2$)$_2$—S$^-$, and —COCH (R$^{16}$)—S; R$^{16}$ is selected from the group consisting of hydrogen, C1–C10 alkyl, C1–C10 aryl, C1–C10 polyhydroxyalkyl, —(CH$_2$)mCO$_2^-$; and (CH$_2$)$_n$NH$_2$; D$^2$ is selected from the group consisting of hydrogen, C1–C10 alkyl, C1–C10 aryl, hydroxyl, C1–C10 polyhydroxyalkyl, C1–C10 alkoxyl, C1–C10 alkoxyalkyl, (CH$_2$)mCO$_2^-$, and —CH$_2$CH$_2$—N(CH$_2$CO$_2^-$)$_2$; Pg is selected from the group consisting of benzoyl, tetrahydropyranyl and methoxycarbonyl and M is a metal ion having an atomic number of 24 to 31, 42 to 49, 58–71, or 74–83.

2. The composition according to claim 1 wherein $R^{17}$ to $R^{21}$ are selected from the group consisting of hydrogen, C1–C10 alkoxyl, —(CH$_2$)m—CO$_2$H$^-$, and —N(R$^6$)(R$^7$); A$^2$ is selected from the group consisting of —O—N(R$^8$)(R$^9$), and —HNCOR$^{11}$, B$^2$ is —CHR$^{13}$, C$^2$ is selected from the group consisting of hydrogen, C1–C10 alkyl, —(CH$_2$) mCO$_2^-$, —CH$_2$CH$_2$—N(CH$_2$CO)$_2$ , and —COCH(R$^{16}$)$_2$— S$^-$; D$^2$ is selected from the group consisting of hydrogen, C1–C10 alkyl, C1–C10 polyhydroxyalkyl, —(CH$_2$)m— CO$_2$, and —CH$_2$CH$_2$—N(CH$_2$CO$_2^-$)$_2$ and M is a metal ion having an atomic number of 24 to 28, 31, 42 to 45, 49, 62–65, 71, 75, 76, or 83.

3. The composition according to claim 1 wherein $R^{17}$ to $R^{21}$ are hydrogens; A$^2$ is —O$^-$ or —N(CH$_2$CO$_2^-$)$_2$; B$^2$ is —CH$_2$—; C$^2$ is selected from the group consisting of —CH$_2$—CO$_2^-$, —CH$_2$CH$_2$—N(CH$_2$CO$_2^-$)$_2$, and —COCH$_2$—S$^-$; D$^2$ is selected from the group consisting of hydrogen, C1–C10 alkyl, and —CH$_2$—CO$_2^-$; and M is a metal ion having an atomic number of 24–26, 28, 31, 43, 44, 49, 62–65, 71, 75, or 76.

4. The composition according to claim 3 wherein $R^{17}$ to $R^{21}$ are hydrogens; A$^2$ is —O$^-$; B$^2$ is —CH$_2$—; C$^2$ is —CH$_2$—CO$_2^-$; D$^2$ is —CH$_2$—CO$_2^-$; and M is a metal ion having an atomic number of 24–26, 31, 44, 49, or 63.

5. The composition according to claim 3 wherein $R^{17}$ to $R^{21}$ are hydrogens; A$^2$ is —O$^-$; B$^2$ is —CH$_2$—; C$^2$ is —COCH$_2$—S$^-$; D$^2$ is hydrogen; and M is a metal ion having an atomic number of 43, 44, 75, or 76.

6. The composition according to claim 3 wherein $R^{17}$ to $R^{21}$ are hydrogens; A$^2$ is —O$^-$; B$^2$ is —CH$_2$—; C$^2$ is —CH$_2$CH$_2$—N(CH$_2$CO$_2^-$)$_2$; D$^2$ is —CH$_2$—CO$_2^-$; and M is a metal ion having an atomic number of 24–26, 44, 49, 62–65, or 71.

7. The composition according to claim 2 wherein $R^{17}$ to $R^{21}$ are hydrogens; A$^2$ is —O$^-$; B$^2$ is —CH$_2$—; C$^2$ and D$^2$ are —CH$_2$CH$_2$—N(CH$_2$CO$_2^-$)$_2$; and M is a metal ion having an atomic number of 24–26, 44, 49, 62–65, or 71.

8. The composition according to claim 3 wherein $R^{17}$ to $R^{21}$ are hydrogens, A$^2$ is —N(CH$_2$CO$_2^-$)$_2$; B$^2$ is —CH$_2$; C$^2$ is CH$_2$CO$_2^-$, D$^2$ is —CH$_2$—CO$_2^-$; and M is a metal ion having an atomic number of 14–16, 44, 49, 62–65, or 71.

* * * * *